US010207449B2

(12) United States Patent
Klausen et al.

(10) Patent No.: US 10,207,449 B2
(45) Date of Patent: Feb. 19, 2019

(54) SEQUENTIAL BIAXIAL STRAIN OF SEMI-CRYSTALLINE TUBES

(71) Applicant: Cook Medical Technologies LLC, Bloomington, IN (US)

(72) Inventors: Kasper Klausen, Helsinge (DK); Alexandra Løvdal, Charlottenlund (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 639 days.

(21) Appl. No.: 14/748,862

(22) Filed: Jun. 24, 2015

(65) Prior Publication Data
US 2015/0367554 A1    Dec. 24, 2015

Related U.S. Application Data

(60) Provisional application No. 62/016,406, filed on Jun. 24, 2014.

(51) Int. Cl.
  *B29C 49/04* (2006.01)
  *B29C 55/26* (2006.01)
  (Continued)

(52) U.S. Cl.
  CPC .............. *B29C 49/04* (2013.01); *A61L 31/04* (2013.01); *A61L 31/14* (2013.01); *A61M 25/0054* (2013.01); *B29C 49/4278* (2013.01); *B29C 49/6472* (2013.01); *B29C 55/26* (2013.01); *B29C 49/0042* (2013.01); *B29K 2067/046* (2013.01); *B29L 2023/00* (2013.01); *B29L 2031/753* (2013.01)

(58) Field of Classification Search
None
See application file for complete search history.

(56) References Cited

U.S. PATENT DOCUMENTS 4,906,244 A  *  3/1990  Pinchuk ................. A61L 29/06
                                                      604/913
4,963,313 A      10/1990  Noddin et al.
                (Continued)

OTHER PUBLICATIONS

A. Mahendrasingam, et al. "Time resolved study of oriented crystallization of poly(lactic acid) during rapid tensile deformation", Sciencedirect.com, Polymer, 46, (2005), pp. 6009-6015.
(Continued)

*Primary Examiner* — Monica A Huson
(74) *Attorney, Agent, or Firm* — Brinks Gilson & Lione

(57) ABSTRACT

The present disclosure provides a processing method for a polymer material to create a medical device with improved mechanical properties. This method allows better tailoring of the material's mechanical properties, hence a device to withstand greater structural loads in vivo. The method comprises providing an extruded polymer tube having an initial diameter and an initial length along a longitudinal direction, and longitudinally, bi-directionally straining the extruded polymer tube in a mold from the initial length to an expanded or extended length. The mold comprises a plurality of stationary heating elements. After longitudinally straining the tube, it is radially expanding in the mold from the initial diameter to an expanded diameter.

15 Claims, 11 Drawing Sheets

(51) Int. Cl.

| | |
|---|---|
| *B29C 49/64* | (2006.01) |
| *B29C 49/42* | (2006.01) |
| *A61M 25/00* | (2006.01) |
| *A61L 31/04* | (2006.01) |
| *A61L 31/14* | (2006.01) |
| *B29K 67/00* | (2006.01) |
| *B29L 31/00* | (2006.01) |
| *B29L 23/00* | (2006.01) |
| *B29C 49/00* | (2006.01) |

(56) References Cited

U.S. PATENT DOCUMENTS

| | | | |
|---|---|---|---|
| 5,156,785 | A | 10/1992 | Zdrahala |
| 5,223,205 | A | 6/1993 | Jackowski et al. |
| 5,728,104 | A | 3/1998 | Trotta |
| 6,248,129 | B1 | 6/2001 | Froix |
| 6,495,090 | B1 | 12/2002 | Wilkins |
| 6,790,225 | B1 | 9/2004 | Shannon et al. |
| 6,986,785 | B2 | 1/2006 | O'Shaughnessy et al. |
| 7,524,445 | B2 | 4/2009 | Duran et al. |
| 7,666,342 | B2 | 2/2010 | Limon et al. |
| 7,806,922 | B2 | 10/2010 | Henderson et al. |
| 7,829,008 | B2 | 11/2010 | Gueriguian et al. |
| 7,901,452 | B2 | 3/2011 | Gale et al. |
| 7,971,333 | B2 | 7/2011 | Gale et al. |
| 8,012,402 | B2 | 9/2011 | Kleiner et al. |
| 8,099,849 | B2 | 1/2012 | Gale et al. |
| 8,268,228 | B2 | 9/2012 | Huang et al. |
| 8,303,296 | B2 | 11/2012 | Kleiner et al. |
| 8,337,739 | B2 | 12/2012 | Wang et al. |
| 8,501,079 | B2 | 8/2013 | Glauser et al. |
| 8,535,372 | B1 | 9/2013 | Fox et al. |
| 8,535,593 | B2 | 9/2013 | Wang et al. |
| 8,545,742 | B2 | 10/2013 | Gada et al. |
| 8,623,069 | B2 | 1/2014 | Hossainy et al. |
| 8,632,847 | B2 | 1/2014 | Pacetti |
| 8,658,081 | B2 | 2/2014 | Gale et al. |
| 8,658,082 | B2 | 2/2014 | Huang et al. |
| 2004/0157024 | A1 | 8/2004 | Colone |
| 2006/0224226 | A1 | 10/2006 | Huang et al. |
| 2007/0253996 | A1 | 11/2007 | Bin et al. |
| 2007/0253999 | A1 | 11/2007 | Huang et al. |
| 2008/0033540 | A1 | 2/2008 | Wang et al. |
| 2009/0146348 | A1 | 6/2009 | Huang et al. |
| 2010/0244304 | A1 | 9/2010 | Wang |
| 2011/0022155 | A1 | 1/2011 | Wang et al. |
| 2011/0062638 | A1 | 3/2011 | Glauser et al. |
| 2011/0066222 | A1 | 3/2011 | Wang et al. |
| 2012/0073733 | A1 | 3/2012 | Ngo et al. |
| 2012/0150283 | A1 | 6/2012 | Kleiner |
| 2012/0277844 | A1 | 11/2012 | Wu |
| 2012/0285609 | A1 | 11/2012 | Wang |
| 2013/0026681 | A1 | 1/2013 | Kleiner et al. |
| 2013/0032967 | A1 | 2/2013 | Wang et al. |
| 2013/0181380 | A1 | 7/2013 | Yang et al. |
| 2013/0187313 | A1 | 7/2013 | Glauser et al. |
| 2013/0241106 | A1 | 9/2013 | Huang et al. |
| 2013/0255853 | A1 | 10/2013 | Wang et al. |
| 2013/0268054 | A1 | 10/2013 | Cottone et al. |
| 2013/0300034 | A1 | 11/2013 | Wang et al. |
| 2013/0310913 | A1 | 11/2013 | Wang et al. |
| 2013/0310921 | A1 | 11/2013 | Lord |
| 2014/0018903 | A1 | 1/2014 | Eli et al. |
| 2014/0033506 | A1 | 2/2014 | Jow et al. |
| 2014/0044860 | A1 | 2/2014 | Castro et al. |
| 2014/0084515 | A1 | 3/2014 | Wang et al. |

OTHER PUBLICATIONS

X. Chen, et al., "Structure Evolution of $\alpha'$-Phase Poly(lactic acid)", Polymer Physics, Journal of Polymer Science Part B: Polymer Phisics, Aug. 9, 2011, 49, pp. 1446-1454.

J. Wu, et al., "Effect of Biaxial Stretching on Thermal Properties, Shrinkage and Mechanical Properties of Poly (Lactic Acid) Films", J. Polym Environ, (2013), 21, pp. 303-311.

S.C. Cifuentes, et al., "Strain rate effect on semi-crystalline PLLA mechanical properties measured by instrumented indentation tests", European Polymer Journal, 59, (2014), pp. 239-246.

A. Løvdal, et al., "Characterization of biaxial strain of poly(L-lactide) tubes", wileyonlinelibrary.com, Polym Int, Society of Chemical Industry, (2015).

S. Sakurai, et al., "Preferential Orientation of Lamellar Microdomains Induced by Uniaxial Stretching of Cross-Linked Polystyrene-*block*-polybutadiene-*block*-polystyrene Triblock Copolymer", Macromolecules, American Chemical Society, (2001), 3-1, pp. 3672-3678.

NatureWorks, "Sheet Extrusion Processing Guide", pp. 1-8.

G. Stoclet, et al., "Strain-Induced Molecular Ordering in Polyactide upon Uniaxial Stretching", Macromolecules, (2010), 43, pp. 1488-1498.

A. Mahendrasingam, et al., "Influence of temperature and chain orientation on the crystallization of poly(ethylene terephthalate) during fast drawing", Polymer, 41, (2000), pp. 7803-7814.

X. Ou, et al. "Influence of biaxial stretching mode on the crystalline texture in polylactic acid films", Polymer, Elsevier.com, ScienceDirect, 49, (2008), pp. 5344-5352.

J. Jagur-Grodzinski, "Polymers for tissue engineering, medical devices, and regenerative medicine. Concise general review of recent studies", Polymers for Advanced Technologies, (2006), 17, pp. 395-418.

M. Tanaka, et al., "Molecular Orientation Distributions in a Biaxially oriented Poly(L-lactic Acid) Film Determined by Polarized Raman Spectroscopy", Biomacromoecules, (2006), 7, pp. 2575-2582.

M. Arnoult, et al., "Mobile amorphous phase fragility in semi-crystalline polymers: Comparison of PET and PLLA", ScienceDirect, Polymer, 8, (2007), pp. 1012-1019.

X. Zhang, et al., "Deformation-mediated superstructures and cavitation of poly (L-lactide): In-situ small-angle X-ray scattering study", Polymer, Elsevier.com, 53, (2012), pp. 648-656.

J. Lee, et al., "Structure development and biodegradability of uniaxially stretched poly(L-lactide)", European Polymer Journal, 37, (2001), pp. 907-914.

D. Rangari, et al., "Study of Strain-Induced Crystallization and Enzymatic Degradation of Drawn Poly(L-lactic acid) (PLLA) Films", Macromolecules, ACS Publications, (2012), pp. 7397-7403.

J. Liu, et al., "Uniaxial stretching of polylactide with different initial crystalline morphologies and temperature effect", European Polymer Journal, Elsevier.com, ScienceDirect, G1, (2014), 83-92.

K. Takahashi, D. Sawai, T. Yokoyama, T. Kanamoto, S. Hyon, Crystal transformation from $\alpha$- to the $\beta$-form upon tensile drawing of poly(L-lactic acid), Polymer, vol. 45, Issue 14, (Jun. 2004).

M.O. Oh, S.H. Kim, Conformational development of polylactide films induced by uniaxial drawing, Polymer International, vol. 63, Edition 7, (2013).

M. Cocca, M. Di Lorenzo, M. Malinconico, V. Frezza, Influence of crystal polymorphism on mechanical and barrier properties of poly(L-lactic acid), European Polymer Journal, vol. 47, Issue 5, (May 2011).

X. Ou, M. Cakmak, Influence of biaxial stretching mode on the crystalline texture in polylactic acid films, Polymer, vol. 49, Issue 24, (Nov. 2008).

X. Ou, M. Cakmak, Comparative study on development of structural hierarchy in constrained annealed simultaneous and sequential biaxially stretched polylactic acid films, Polymer, vol. 51, Issue 3, (Feb. 2010).

G. Stoclet, R. Seguela, J.M. Lefebvre, S. Elkoun, C. Vanmansart, Strain-Induced Molecular Ordering in Polylactide upon Uniaxial Stretching, Macromolecules, vol. 43, Issue 3, (2010).

G. Stoclet, R. Seguela, C. Vanmansart, C. Rochas, J.M. Lefebvre, WAXS study of the structural reorganization of semi-crystalline polylactide under tensile drawing, Polymer, vol. 53, Issue 2, (Jan. 2012).

Xiaolang Chen, Jeffrey Kalish, Shaw Ling Hsu, Structure evolution of $\alpha$-phase Poly(lactic acid), Journal of Polymer Science Part B: Polymer Physics, vol. 49, Issue 20, (Oct. 2011).

(56) References Cited

OTHER PUBLICATIONS

X. Zhang, K. Schneider, G. Liu, J. Chen, K. Brüning, D. Wang, M. Stamm, Deformation-mediated superstructures and cavitation of poly ($_L$-lactide): In-situ small-angle X-ray scattering study, Polymer, vol. 53, (2012).

X. Zhang, K. Schneider, G. Liu, J. Chen, K. Brüning, D. Wang, M. Stamm, Structure variation of tensile-deformed amorphous poly(L-lactic acid): Effects of deformation rate and strain, Polymer, vol. 52, (2011).

K.M. Nampoothiri, N.R. Nair, R.P. John, An overview of the recent developments in polylactide (PLA) research, Bioresource Technology, vol. 101, Issue 22, (Nov. 2010).

J.C. Velazquez-Infante, J. Gamez-Perez, E.A. Franco-Urquiza, O.O. Santana, F. Carrasco, M. Li Maspoch, Effect of the Unidirectional Drawing on the Thermal and Mechanical Properties of PLA Films with Different L-Isomer Content, Journal of Applied Polymer Science, vol. 127, Issue 4, (Feb. 2013).

S.C. Lee, J.I. Han, J.W. Heo, Endotherm just above glass transition in uniaxially drawn poly(lactic acid)s films with various D-isomer contents, Polymer, vol. 54, No. 14, (2013).

F. Carrasco, P. Pagès, J. Gámez-Péres, O.O. Santana, M.L. Maspoch, Processing of poly(lactic acid): Characterization of chemical structure, thermal stability and mechanical properties, Polymer, vol. 95, No. 2, (2010).

Y. Wang, S.S. Funari, J.F. Mano, Influence of semicrystalline Morphology on the Glass transition of Poly(L-lactic acid), Macromol. Chem. Phys., vol. 207, Issue 14, (Jul. 2006).

L.T. Lim, R. Auras, M. Rubino, Processing technologies for poly(lactic acid), Progress in Polymer Science, vol. 33, Issue 8, (Aug. 2008).

C. Tsai, R. Wu, H. Cheng, S. Li, Y. Siao, D. Kong, Crystallinity and dimensional stability of biaxial oriented poly(lactic acid) films, Polymer Degradation and Stability, vol. 95, Issue 8, (Aug. 2010).

J. Wu, M. Yen, C. Wu, C. Li, M.C. Kuo, Effect of biaxial stretching on thermal properties, shrinkage and mechanical properties of poly(Lactic Acid) films, J Polym Environ, vol. 21, Issue 1, (Mar. 2013).

N.A. Weir, F.J. Buchanan, J.F. Orr, D.F. Farrar, A. Boyd, Processing, annealing and sterilisation of poly-L-lactide, Biomaterials, vol. 25, No. 18, (Aug. 2004).

A. Saeidlou, M.A. Huneault, H. Li, C.B. Park, Poly(lactic acid) crystallization, Progress in Polymer Science, vol. 37, Issue 12, (Dec. 2012).

S Sakurai, S Aida, S Okamoto, T Ono, K Imaizimu and S Nomura, Preferential Orientation of Lamellar Microdomains Induced by Uniaxial Stretching of Cross-Linked Polystryrene-*block*-polybutadiene-*block*-polystyrene Triblock Copolymer, Macromolecules, vol. 34, Issue 11 (Apr. 2001).

D. Apitz, R. P. Bertram, N. Benter, W. Hieringer, J. W. Andreasen, M. M. Nielsen, P. M. Johansen, and K. Buse, Investigation of chromophore-chromophore interaction by electro-optic measurements, linear dichroism, x-ray scattering, and density-functional calculations, Phys. Rev. E, vol. 72, No. 3, Part 2, (Sep. 2005).

L. Nair, C. Laurencin, Biodegradable polymers as biomaterials, ScienceDirecy, Prog. Polym. Sci., 32 (2007).

G. Stoclet, R. Seguela, J. Lefebvre, Morphology, thermal behavior and mechanical properties of binary blends of compatible biosourced polymers: Polylactide/polyamide11, ScienceDirect, Polymer 52 (2011).

A. Lasprilla, G. Martinez, B. Lunelli, A. Jardini, R. Filho, Poly-lactic acid synthesis for application in biomedical devices—A review, ScienceDirect, Biotechnology Advances 30 (2012).

J. Zhang, Y. Duan, H. Sato, H. Tsuji, I. Noda, S. Yan, Y. Ozaki, Crystal Modifications and Thermal Behavior of Poly(L-lactic acid) Revealed by Infrared Spectroscopy, Macromolecules (2005).

J. Hébert, P. Wood-Adams, M. Heuzey, C. Dubois, J. Brisson, Morphology of Polyactic Acid Crystallized during Annealing after Uniaxial Deformation, Polymer Physics, Wiley Periodicals, Inc. (2012) materialsview.com, Journal of Polymer Science, Part B: Polymer Physics 2013.

A. Løvdal, L. Laursen, T. Andersen, B. Madsen, L. Mikkelsen, Influence of Temperature on Mechanical Properties of Jute/Biopolymer Composites, Journal of Applied Polymer Science, Wiley Periodicals, Inc. 2012.

Z. Xiong, G. Liu, X. Zhang, T. Wen, S. de Vos, C. Joziasse, D. Wang, Temperature dependence of crystalline transition of highly-oriented poly ($_L$-lactide)/poly($_D$-lactide) blend: In-Situ synchrotron X-ray scattering study, SciVerse ScienceDirect, Polymer 54 (2013).

N. Delpouve, L. Delbreilh, G. Stoclet, A. Saiter, E. Dargent, Structural Dependence of the Molecular Mobility in the Amorphous Fractions of Polylactide, Macromolecules, ACS Publications, American Chemical Society (2014).

H. Tsuji, Y. Ikada, Properties and morphologies of poly ($_L$-lactide): 1. Annealing condition effects on properties and morphologies of poly ($_L$-lacitde), Butterworth Heinemann, Polymer, vol. 36, No. 14 (1995).

T. Kawai, N. Rahman, G. Matsuba, K. Nishida, T. Kanaya, M. Nakano, H. Okamoto, J. Kawada, A. Usuki, N. Honma, K. Nakajima, M. Matsuda, Crystalization and Melting Behavior of Poly (L-lactic Acid), Macromolecules 40 (2007).

A. Mahendrasingam, D. Blundell, M. Parton, A. Wright, J. Rasburn, T. Narayanan, W. Fuller, Time resolved study of oriented crystallization of poly(lactic acid) during rapid tensile deformation, Science Direct, Polymer 46 (2005), pp. 6009-6015.

X. Chen, J. Kalish, S. Hsu, Structure Evolution of α-Phase Poly(lactic acid), Journal of Polymer Science Part B: Polymer Physics, (2011), 49, pp. 1446-1454.

K. Takahashi, D. Sawai, T. Yokoyama, T. Kanamoto, S. Hyon, Crystal transformation from α- to the β-form upon tensile drawing of poly(L-lactic acid), Polymer, vol. 45, Issue 14, (Jun. 2004), pp. 4969-4976. Abstract.

M.O. Oh, S.H. Kim, Conformational development of polylactide films induced by uniaxial drawing, Polymer International, vol. 63, Edition 7, (2013), pp. 1247. Abstract.

M. Cocca, M. Di Lorenzo, M. Malinconico, V. Frezza, Influence of crystal polymorphism on mechanical and barrier properties of poly(L-lactic acid), European Polymer Journal, vol. 47, Issue 5, (May 2011), pp. 1073-1080. Abstract.

X. Ou, M. Cakmak, Influence of biaxial stretching mode on the crystalline texture in polylactic acid films, Polymer, vol. 49, Issue 24, (Nov. 2008), pp. 5344-5352. Abstract.

X. Ou, M. Cakmak, Comparative study on development of structural hierarchy in constrained annealed simultaneous and sequential biaxially stretched polylactic acid films, Polymer, vol. 51, Issue 3, (Feb. 2010), pp. 783-792. Abstract.

G. Stoclet, R. Seguela, J.M. Lefebvre, S. Elkoun, C. Vanmansart, Strain-Induced Molecular Ordering in Polylactide upon Uniaxial Stretching, Macromolecules, vol. 43, Issue 3, (2010), pp. 1488-1498. Abstract.

G. Stoclet, R. Seguela, C. Vanmansart, C. Rochas, J.M. Lefebvre, WAXS study of the structural reorganization of semi-crystalline polylactide under tensile drawing, Polymer, vol. 53, Issue 2, (Jan. 2012), pp. 519-528. Abstract.

G Stoclet, R Seguela, J M Lefebvre, S Li, M Vert, Thermal and Strain-Induced Chain Ordering in Lactic acid Stereocopolymers: Influence of the composition in Stereomers, Macromolecules, vol. 44, Issue 12, (2011), pp. 4961-4969. Abstract.

Xiaolang Chen, Jeffrey Kalish, Shaw Ling Hsu, Structure evolution of α-phase Poly(lactic acid), Journal of Polymer Science Part B: Polymer Physics, vol. 49, issue 20, (Oct. 2011), pp. 1446-1454. Abstract.

X. Zhang, K. Schneider, G. Liu, J. Chen, K. Bruning, D. Wang, M. Stamm, Deformation-mediated superstructures and cavitation of poly ($_L$-lactide): In-situ small-angle X-ray scattering study, Polymer, vol. 53, (2012), pp. 648-656. Abstract.

X. Zhang, K. Schneider, G. Liu, J. Chen, K. Brüning, D. Wang, M. Stamm, Structure variation of tensile-deformed amorphous poly(L-lactic acid): Effects of deformation rate and strain, Polymer, vol. 52, (2011), pp. 4141-4149. Abstract.

K.M. Nampoothiri, n. R. Nair, R.P. John, an overview of the recent developments in polylactide (PLA) research, Bioresource Technology, vol. 101, Issue 22, (Nov. 2010), pp. 8493-8501. Abstract.

(56) References Cited

OTHER PUBLICATIONS

J.C. Velazquez-Infante, J. Gamez-Perez, E.A. Franco-Urquiza, O.O. Santana, F. Carrasco, M. Li Maspoch, Effect of the Unidirectional Drawing on the Thermal and Mechanical Properties of PLA Films with Different L-Isomer Content, Journal of Applied Polymer Science, vol. 127, Issue 4, (Feb. 2013), pp. 2661-2669. Abstract.

S.C. Lee, J.I. Han, J.W. Heo, Endotherm just above glass transition in uniaxially drawn poly(lactic acid)s films with various D-isomer contents, Polymer, vol. 54, No. 14, (2013), pp. 3624-3632. Abstract.

F. Carrasco, P. Pagès, J. Gáméz-Peres, O.O. Santana, M.L. Maspoch, Processing of poly(lactic acid): Characterization of chemical structure, thermal stability and mechanical properties, Polymer, vol. 95, No. 2, (2010), pp. 116-125. Abstract.

Y. Wang, S.S. Funari, J.F. Mano, Influence of semicrystalline Morphology on the Glass transition of Poly(L-lactic acid), Macromol. Chem. Phys., vol. 207, Issue 14, (Jul 2006), pp. 1262-1271. Abstract.

L.T. Lim, R. Auras, M. Rubino, Processing technologies for poly(lactic acid), Progress in Polymer Science, vol. 33, Issue 8, (Aug. 2008), pp. 820-852. Abstract.

C. Tsai, R. Wu, H. Cheng, S. Li, Y. Siao, D. Kong, Crystallinity and dimensional stability of biaxial oriented poly(lactic acid) films, Polymer Degradation and Stability, vol. 95, Issue 8, (Aug. 2010), pp. 1292-1298. Abstract.

J. Wu, M. Yen, C. Wu, C. Li, M.C. Kuo, Effect of biaxial stretching on thermal properties, shrinkage and mechanical properties of poly(Lactic Acid) films, J Polym Environ, vol. 21, Issue 1, (Mar. 2013), pp. 303-311. Abstract.

N.A. Weir, F.J. Buchanan, J.F. Orr, D.F. Farrar, A. Boyd, Processing, annealing and sterilisation of poly-L-lactide, Biomaterials, vol. 25, No. 18, (Aug. 2004), pp. 3939-3949. Abstract.

A. Saeidlou, M.A. Huneault, H. Li, C.B. Park, Poly(lactic acid) crystallization, Progress in Polymer Science, vol. 37, Issue 12, (Dec. 2012), pp. 1657-1677. Abstract.

S Sakurai, S Aida, S Okamoto, T Ono, K Imaizimu and S Nomura, Preferential Orientation of Lamellar Microdomains Induced by Uniaxial Stretching of Cross-Linked Polystryrene-*block*-polybutadiene-*block*-polystyrene Triblock Copoplymer, Macromolecules, vol. 34, Issue 11 (Apr. 2001), pp. 3672-3678. Abstract.

D. Apitz, R. P. Bertram, N. Benter, W. Hieringer, J. W. Andreasen, M. M. Nielsen, P. M. Johansen, and K. Buse, Investigation of chromophore-chromophore interaction by electro-optic measurements, linear dichroism, x-ray scattering, and density-functional calculations, Phys. Rev. E, vol. 72, No. 3, Part 2, (Sep. 2005). Abstract.

Cardinal Search Report dated May 20, 2014.

\* cited by examiner

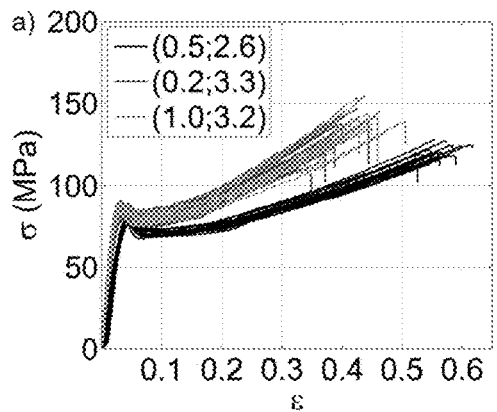 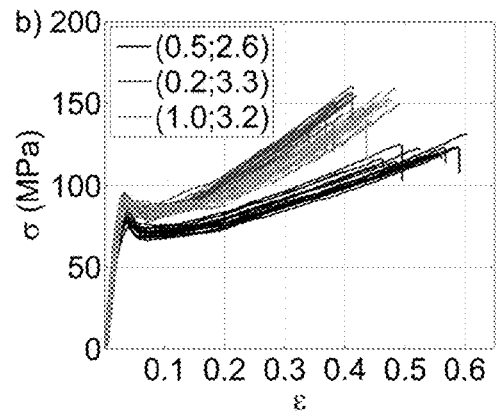
Figure 5A　　　　　　　　　　Figure 5B
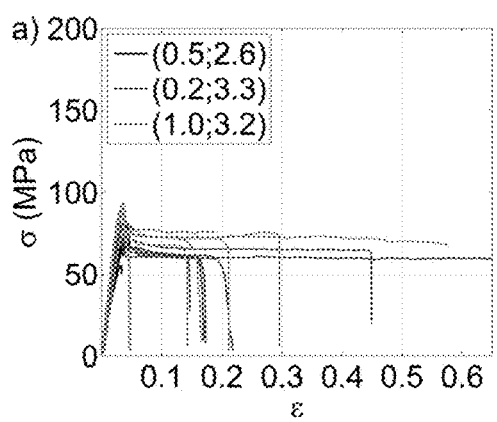 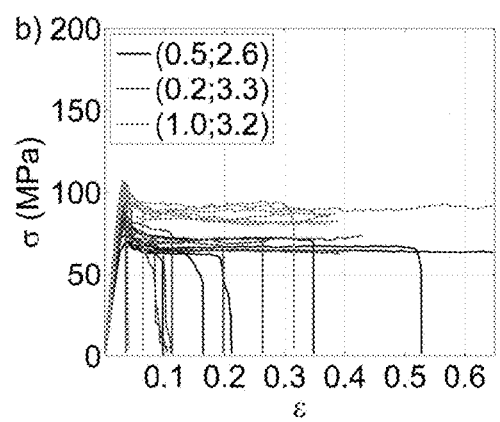
Figure 6A　　　　　　　　　　Figure 6B

| | $(\varepsilon_a; \varepsilon_r)$ | $E_{20-40 \text{ (circ)}}$ | $\sigma_{y \text{ (circ)}}$ | $\sigma_{max \text{ (circ)}}$ | $E_{20-40 \text{ (axial)}}$ | $\sigma_{y \text{ (axial)}}$ |
|---|---|---|---|---|---|---|
| SIM | (0.2;2.6) | 3274±198 | 77±2 | 119±10 | 2320±273 | 67±7 |
| SIM | (0.5;2.6) | 3456±195 | 78±2 | 119±8 | 2614±219[b] | 76±6[b] |
| SIM | (0.2;3.3) | 3834±292[a] | 86±3[a] | 131±10[a,b] | 2983±174[b] | 80±6[b] |
| SIM | (1.0;3.2) | 3997±255[a] | 87±3[a] | 137±9[a,b] | 2848±189[a,b] | 77±3[a,b] |
| SIM(90°C) | (1.0;3.2) | 2963±338 | 78±5 | 140±12 | 1961±196 | 67±3 |
| SEQ | (0.5;2.6) | 3460±258 | 82±5 | 128±13 | 2983±174[b] | 80±6 |
| SEQ | (0.2;3.3) | 3946±321[a] | 89±4[a] | 144±13[a,b] | 3197±143[a,b] | 86±5[b] |
| SEQ | (1.0;3.2) | 3964±283[a] | 91±4[a] | 150±9[a,b] | 3966±275[a,b] | 102±3[a,b] |
| SEQ(90°C) | (1.0;3.2) | 2821±217 | 77±3 | 136±13 | 2028±196 | 83±11 |

Figure 9

| | $(\varepsilon_a; \varepsilon_r)$ | Xc (%) | $T_g$ (°C) | $(D_c)$ (Å) | $(D_a)$ (Å) |
|---|---|---|---|---|---|
| As extruded | (0) | 1 | 62 | - | - |
| SIM | (0.2;2.6) | 30 | 62 | 67 | 160 |
| SIM | (0.5;2.6) | 32 | 63 | 70 | 151 |
| SIM | (0.2;3.3) | 29 | 66 | 69 | 139 |
| SIM | (1.0;3.2) | 31 | 65 | 65 | 137 |
| SIM(90°C) | (1.0;3.2) | 28 | 65 | 65 | 141 |
| SEQ | (0.5;2.6) | 29 | 64 | 63 | 160 |
| SEQ | (0.2;3.3) | 30 | 65 | 63 | 146 |
| SEQ | (1.0;3.2) | 32 | 65 | 60 | 129 |
| SEQ(90°C) | (0.5;2.6) | 30 | 65 | 45 | 142 |
| UNI | (1.0;0) | 34 | 61 | 183 | 62 |
| UNI (120°C) | (1.0;0) | 36 | 60 | 160 | 126 |
| ISO (90 °C) | (0) | 29 | 61 | 62 | 136 |

Figure 10

|  | ($\varepsilon_a$; $\varepsilon_r$) | (103) 2θ(°) | (010) 2θ(°) | (110/200) 2θ(°) | (203) 2θ(°) | (015) 2θ(°) | (206) 2θ(°) | (018) 2θ(°) |
|---|---|---|---|---|---|---|---|---|
| SIM | 0.5;3.0 | | | 16.5 | 19.1 | | 24.8 | 33.0 |
| SIM | 0.2;4.3 | | | 16.5 | 18.7 | | 24.5 | 32.7 |
| SIM | 1.0;4.3 | | | 16.2 | 18.8 | | 24.3 | 32.4 |
| SIM (90°C 60min) | | | | | | | | 32.72 |
| SEQ | 0.5;3.0 | | | 15.1 | 17.3 | | 22.8 | 30.4 |
| SEQ | 0.2;4.3 | | | 15.3 | 17.3 | | 22.8 | 30.4 |
| SEQ | 1.0;4.3 | | | 15.1 | 17.3 | | 22.8 | 30.4 |
| SEQ (90°C 60min) | | | | | | | | 32.4 |
| UNI | 1.0;0 | | | 15.2 | 17.1 | | 22.5 | |
| ISO | | 12.5 | 14.8 | 16.8 | 19.1 | 22.2 | | |
| α (chen et al 2011, wang et al 2006) | | 12.6 | 14.8-15.0 | 16.7 | 19.1 | 22.2 | | |
| α'(chen et al 2011, wang et al 2006) | | | | 16.6 | 18.9 | | 24.7 | 33.1 |

| | $X_c$ (%) | Total Area Expansion (%) |
|---|---|---|
| Sequential biaxial strained | 30 | 432 |
| Simultaneous biaxial strained | 29 | 432 |
| Only axial strain | 34 | - |

SEQUENTIAL BIAXIAL STRAIN OF SEMI-CRYSTALLINE TUBES

CROSS-REFERENCE TO RELATED APPLICATIONS

This application claims priority to U.S. Provisional Patent Application Ser. No. 62/016,406, filed Jun. 24, 2014, entitled "SEQUENTIAL BIAXIAL STRAIN OF SEMI-CRYSTALLINE TUBES," the entire contents of which are hereby incorporated by reference.

BACKGROUND

1. Technical Field Text

The present disclosure relates to medical devices. More particularly, the disclosure relates to a processing method and final product involving sequential biaxial straining of semi-crystalline tubes to prepare medical devices.

2. Background Information

Medical devices, such as stents and filters, need to withstand structural loads when placed within the vasculature of a patient. How well these devices withstand structural loads relates to both the mechanical properties of the material used to make the device and the device design.

Without sufficient mechanical properties, a medical device made from such a material may deform or fracture when placed in the vasculature and cause other later complications. A device should have sufficient strength to maintain its size and shape in vivo. Such devices may be formed from polymers.

Semi-crystalline polymers have crystalline domains and amorphous domains. Crystalline domains have highly ordered polymer chains. Contrastingly, amorphous domains may have a more random orientation of polymer chains. In order to improve the mechanical properties of semi-crystalline polymers, it is known to cause strain induced crystallinity. Strain induced crystallinity induces alignment of polymer chains in the direction of the strain. Strain induced crystallinity can improve mechanical properties in the direction of the strain, but there is a need for new methods to further improve mechanical properties in all directions.

Likewise, there is a need for further straining methods to adjust method steps as needed. For example, it may be advantageous to modify polymer chain orientation in multiple directions during the method. As such, there exists a need for further straining methods.

BRIEF SUMMARY

The present disclosure provides a processing method for a polymer material with sequential steps such that the user can tailor the molecular orientation at each step, as desired. Such tailoring may create a medical device with improved mechanical properties. This method may allow the material and device to withstand greater structural loads in vivo. The present disclosure also provides for a method to independently manipulate or alter material properties in different directions or along two different axes (e.g. radially and longitudinally).

The method may comprise longitudinally straining an extruded polymer tube in a mold, the extruded polymer tube having an initial diameter, an initial length, and a lumen therethrough along a longitudinal direction. The extruded polymer tube may be longitudinally strained from the initial length to an extended length. The mold may include a plurality of stationary heating elements. After the step of longitudinally straining an extruded polymer tube, the extruded polymer tube may be radially expanded in the mold wherein the extruded polymer tube is expanded from the initial diameter to an expanded diameter.

The step of longitudinally straining an extruded polymer tube may include straining the extruded polymer tube to the extended length being about 20% to about 200% greater than the initial length. The method may further include extruding a polymer material through a tubular die to define the extruded polymer tube before the step of longitudinally straining an extruded polymer tube. The polymer material may be poly-(L-lactic) acid. The initial length of the heated section of the initial, extruded polymer tube may be about 10, about 25, about 50, about 75, or about 100 millimeters.

The method may include disposing the extruded polymer tube into the mold before the step of longitudinally straining an extruded polymer tube. The step of disposing the extruded polymer tube may include positioning the plurality of stationary heating elements circumferentially about the extruded polymer tube in the mold. The method may include heating the extruded polymer tube to a first temperature before the step of longitudinally straining an extruded polymer tube. The first temperature may be between a glass transition temperature and a cold crystallinity temperature of the polymer material; the first temperature range may be above the glass transition temperature to below the cold crystallinity temperature. In one embodiment, the first temperature is between about 74° C. to about the cold crystallinity temperature. In another embodiment, the first temperature is about 90° C.

The method may further include cooling the extruded polymer tube to a second temperature after the step of longitudinally straining an extruded polymer tube and before the step of radially expanding the extruded polymer tube. The second temperature may be any temperature that is different from the first temperature. In one example, the second temperature may be below the first temperature and above the glass transition temperature. Preferably, the second temperature is about 74° C. In some embodiments, radially expansion of the extruded polymer tube may include expanding the initial diameter in the range of about 100% to about 500%, defining the expanded diameter. In some cases, the expansion may be to at or above 300% (e.g. about 430%)

The method may further include pressurizing the lumen of the extruded polymer tube after the step of longitudinally straining an extruded polymer tube and before the step of radially expanding the extruded polymer tube, the step of pressurizing the lumen may include increasing from a first pressure to a second pressure with a gas, wherein the first pressure is about atmospheric pressure and the second pressure is between about 2 bar and about 25 bar. The method may further include cooling the extruded polymer tube to a third temperature to define a processed polymer tube after the step of radially expanding the extruded polymer tube.

The method may further include cutting the processed polymer tube to define a medical device. The processed polymer tube may have a lower crystal orientation in the longitudinal direction, or along the longitudinal axis, than the extruded polymer tube after the step of longitudinally straining.

The disclosure also provides for a medical device having a tubular body formed from an extruded polymer tube that is longitudinally strained in a mold. The extruded polymer tube has an initial diameter, an initial length, and a lumen therethrough along a longitudinal axis or direction, wherein the extruded polymer tube is longitudinally strained from the initial length to an extended length after which a transverse strain is applied, the expansion.

The extruded polymer tube may also be radially expanded in the mold wherein the extruded polymer tube is expanded from the initial diameter to an expanded diameter after the extruded polymer tube has been longitudinally strained. This may involve using the processing method described herein.

By this processing, the tubular body may have an elastic modulus along the longitudinal axis or in the longitudinal direction of above 3500 megapascals ("MPa"), more preferably, about 4000 megapascals. In addition, the tubular body may have a yield stress in the longitudinal direction of above 90 megapascals after processing, more preferably, about 100 megapascals.

BRIEF DESCRIPTION OF THE DRAWINGS

FIGS. 5A-B depict stress/strain curves for processed tubes, measured in the circumferential direction;

FIGS. 6A-B depict stress/strain curves for processed tubes, measured in the axial direction;

FIG. 9 is a table depicting the elastic modulus, $\sigma_y$, $\sigma_{max}$ of processed tubes;

FIG. 10 is a table depicting crystallinity percentages ($X_c$) and crystallite sizes for both the circumferential ($D_c$) and the axial direction ($D_a$);

DETAILED DESCRIPTION

Figure 1:
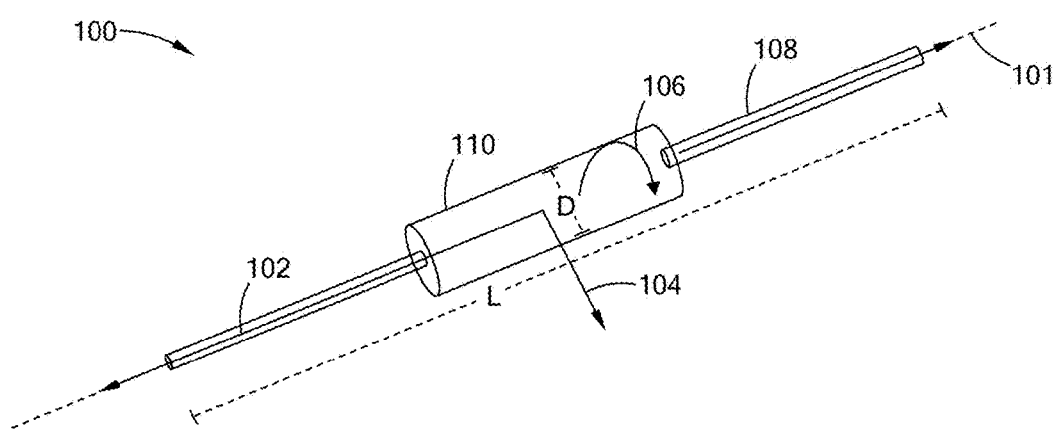
FIG. 1 is a side view of a semi-crystalline tube processed by a sequential biaxial strain method in accordance with one embodiment of the present disclosure.

The present disclosure provides a process for performing sequential biaxial strain ("SEQ") of a semi-crystalline polymer tube. The accompanying figures are provided for general understanding of the structure of various embodiments. However, this disclosure may be embodied in many different forms. These figures should not be construed as limiting and they are not necessarily to scale.

All publications, patent applications, patents and other references mentioned herein are incorporated by reference in their entirety. Unless otherwise defined, all technical and scientific terms used herein have the same meaning as commonly understood by one of ordinary skill in the art to which this invention pertains. In case of conflict, the present document, including definitions, will control.

"About" or "approximately" referred to herein to describe a given quantity mean within 10%, preferably within 5%, more preferably within 1%. For example, if an initial length of an extruded polymer tube is about 50 millimeters that means within about 10%, preferably within 5%, more preferably within 1%, of 50 millimeters.

"Axial" and "longitudinal" referred to herein are a direction of a tube, running along the tube axis. They may be used interchangeably in this application.

"Circumferential" referred to herein is the direction running around the circumference of the polymer tube.

"Cold crystallinity temperature," "$T_{cc}$," referred to herein is the temperature at which crystals form in the polymer material when heated from cold. For example, this can occur when crystals form as the polymer material is being heated.

"Crystal orientation" referred to herein relates to the aligning and folding of polymer chains with neighboring polymer chains within a crystalline domain of a polymer material. This can be contrasted with the "amorphous orientation," which may contain random polymer chains. In such amorphous orientation, the polymer chains may be more disordered, irregular, and entangled with respect to neighboring polymer chains than the crystalline domains.

"Glass transition temperature," "$T_g$," referred to herein is the temperature at which the amorphous domains change from a brittle, glassy state to a rubber-like state.

"Mechanical properties" referred to herein are the stiffness and strength in the of the polymer material, usually in the form of a tube or a tubular specimen. Mechanical properties may be measured in the circumferential direction or along the longitudinal axis of the tube.

"Melting temperature," "$T_m$," referred to herein in the temperature at which a material undergoes a phase change from solid to liquid.

"Polymer chain orientation" referred to herein relates to the direction and arrangement of polymer chains with respect to neighboring polymer chains.

"Radial" referred to herein is the direction radiating from the center of a tube towards the circumference of the tube.

"Strain" referred to herein is the degree of expansion or deflection that occurs in a material at any given stress or load. Longitudinal strain may be expressed as a percentage or fraction of the original length. Strain therefore is positive for expansion.

FIG. 1 is a side view of a semi-crystalline tube processed by a sequential strain method. The semi-crystalline tube 100 is extruded from a polymer material into, or to define, an extruded polymer tube. The semi-crystalline tube or extruded polymer tube 100 has a radially expanded segment 110 shown with perpendicular and parallel arrows in the direction of processing strains.

The semi-crystalline tube 100 generally has a length L running along the longitudinal axis 101 of the tube, and a diameter D running to the circumference 106. First, the tube undergoes an axial or longitudinal strain along a longitudinal axis 101. This strain is bi-directional in that it occurs both in the direction of arrow 102 and the direction of arrow 108, i.e. opposite, or positive and negative, directions. As such a "longitudinal strain" may be "a bi-directional" strain. This strain increases the overall length of the tube from an initial length to an extended length.

Next, the tube undergoes a radial expansion in the direction of arrow 104. This increases the diameter of the tube from an initial diameter to an expanded diameter. The longitudinally strained and radially expanded tube is cooled, resulting in a processes polymer tube. The method may improve the mechanical properties and strength in the circumferential direction 106.

Figure 2:
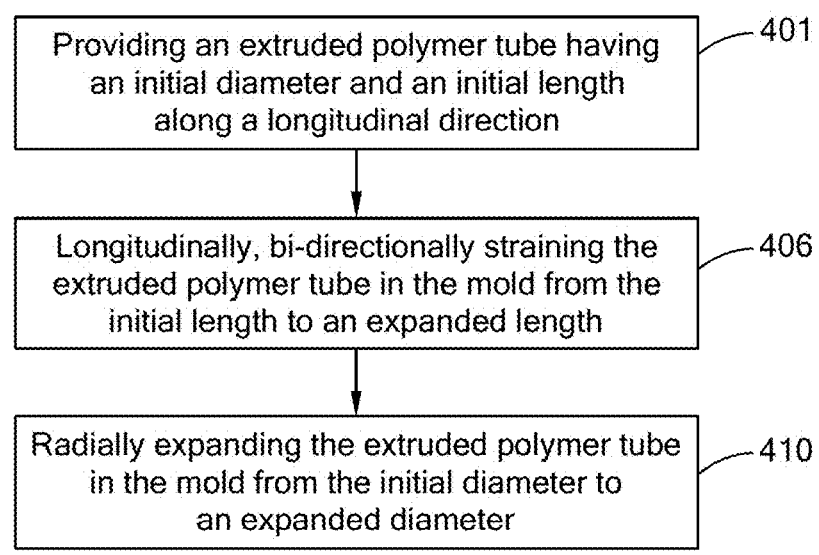
FIG. 2 is a flow diagram of the sequential biaxial strain method in accordance with one embodiment of the present disclosure.

FIG. 2 provides a flow diagram of one embodiment of the sequential biaxial strain method. This flow diagram may be an abbreviated method. In step 401, the user provides or obtains an extruded polymer tube having initial diameter and initial length along a longitudinal direction or axis. In step 406, the user longitudinally strains the extruded polymer tube in a mold from the initial length to an extended or expanded length. In step 410, the user then radial expands the extruded polymer tube in the mold from the initial diameter to the expanded diameter by applying a pressure.

Figure 3A:
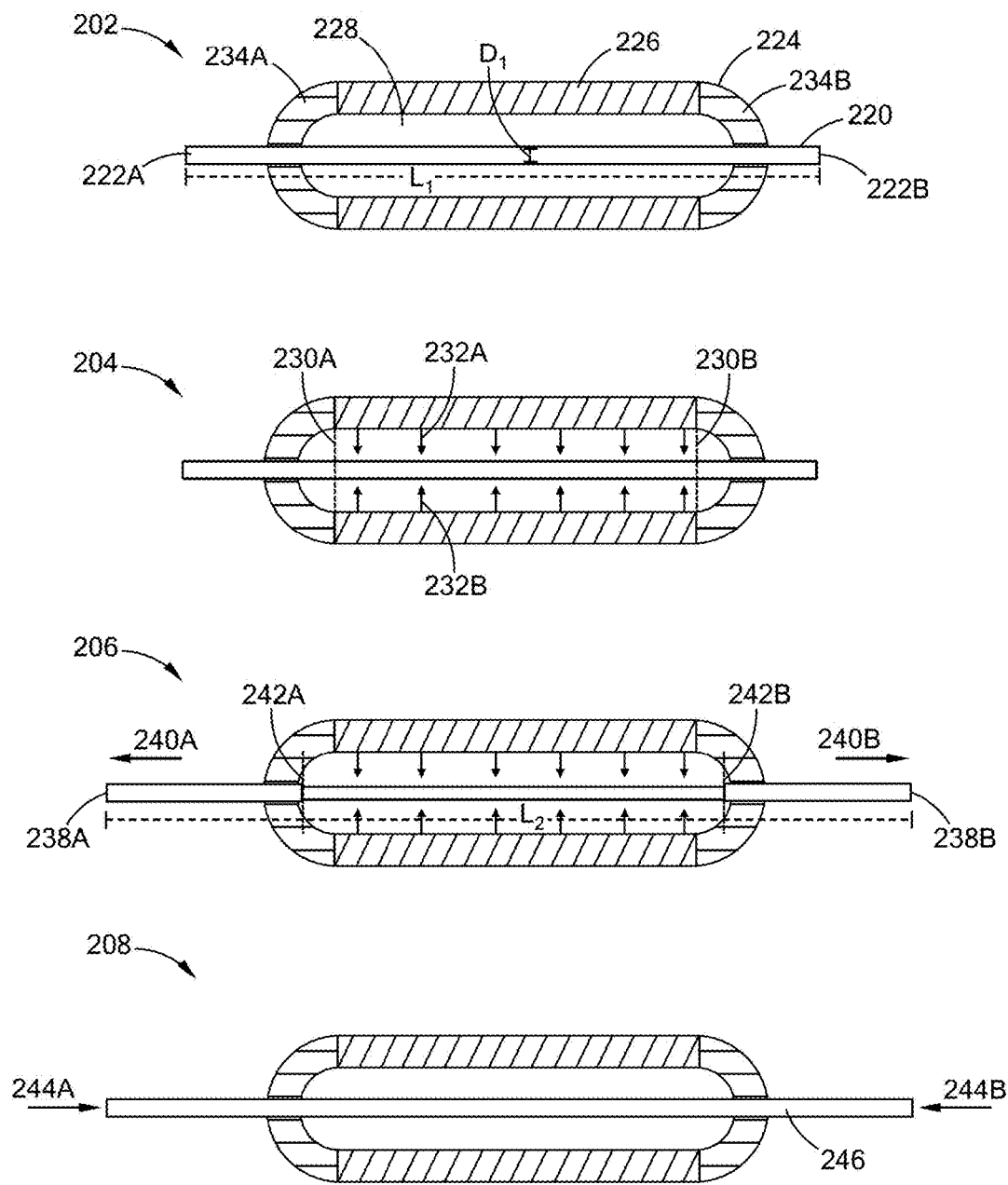
FIGS. 3A-B are steps of the sequential biaxial strain method in accordance with one embodiment of the present disclosure.
Figure 3B:
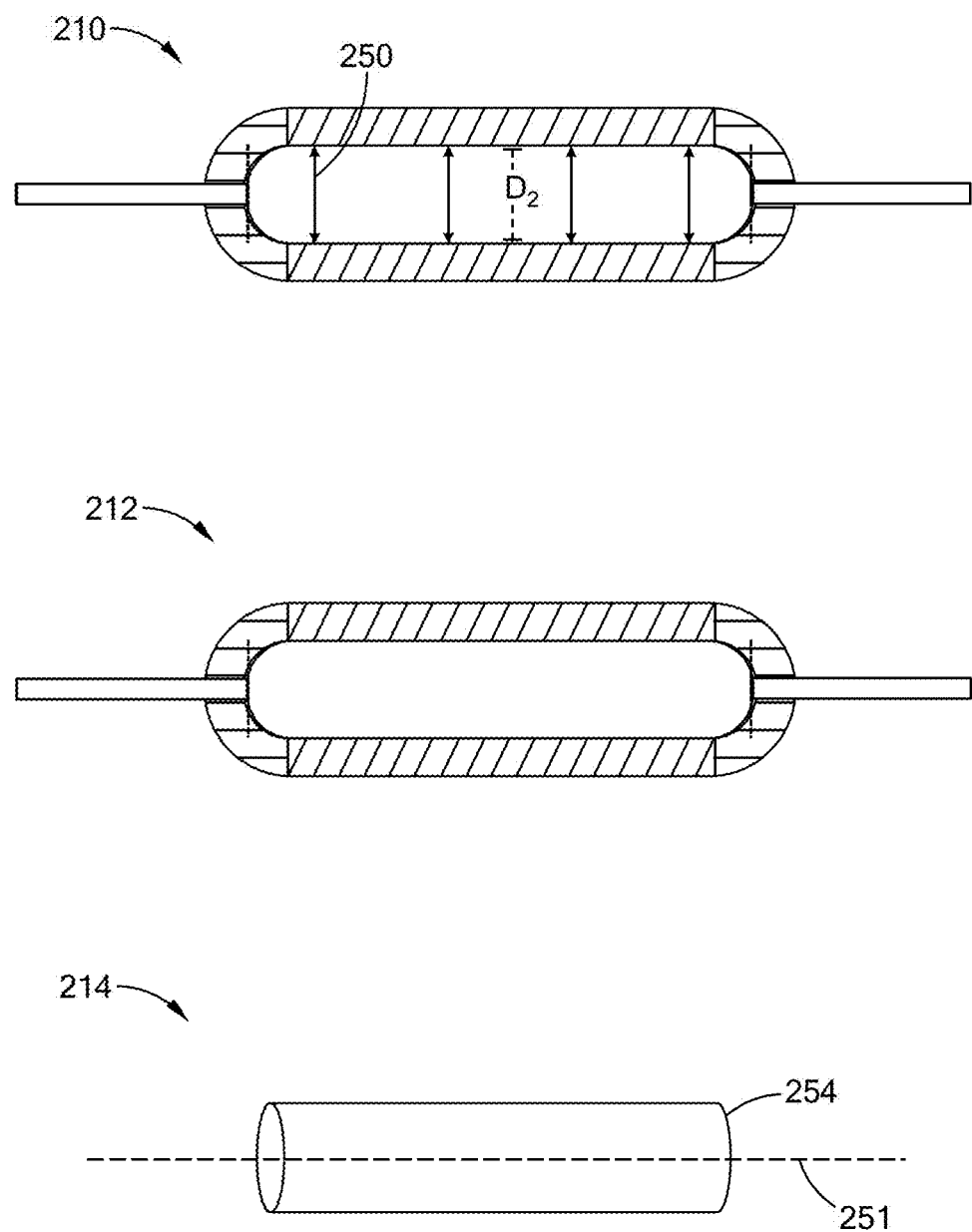

FIGS. 3A-3B show further steps of the sequential straining method. These steps move from the abbreviated steps shown in FIG. 2 to a more expanded method, also described in FIG. 4.

In step 202, a polymer material may be extruded through a tubular die, forming or defining a semi-crystalline tube or extruded polymer tube 220. This extruded polymer tube 220 has an initial length $L_1$, initial diameter $D_1$, and a lumen therethrough along a longitudinal direction of the tube. At this point, the extrusion process creating the polymer tube may have oriented the polymer chains in the longitudinal direction along the longitudinal axis. Extrusion may create higher mechanical properties of the polymer material in the longitudinal direction, but also may create lower mechanical properties of the polymer material in the circumferential direction.

A skilled artisan may employ many different types of semi-crystalline polymers for the polymer material in this process. Preferably, the semi-crystalline polymer will have both low initial crystallinity and low crystal orientation. By the end of the process, the crystallinity may increase, but the crystal orientation may decrease overall. In one embodiment, the polymer material is poly-(L-lactic) acid with an initial crystallinity below 5%. The polymer material may also be poly-(L-lactic) acid ("PLLA"), poly-(D-lactic) acid ("PDLA"), polyglycolic acid, or polycaprolactone, and derivatives thereof.

It may be advantageous to process the selected polymer (e.g. PLLA) to achieve strain-induced amorphous orientation and packing of crystals. Both the physical and mechanical properties of polymers (e.g. PLLA) may be improved through processing, and may depend on the structure of the polymer, including its crystal morphology. By using a sequential processing, the inventors found that this processing method allows for better control of polymer orientation while processing a polymer material. As such, the process may be tailored to specific polymers to provide specific polymer chain orientation.

After processing (e.g. FIGS. 5-16), the inventors investigated changes in crystallinity, crystal size, and orientation of chains to determine effects of the processing method (e.g. FIG. 3A-B) on some mechanical properties (e.g. elastic modulus and yield stress). In particular, PLLA has shown promise to be a replacement of petrol based polyesters, and PLLA may benefit from improved physical and mechanical properties.

Returning to FIG. 3A, once the user selects and extrudes the desired polymer material, the user may then dispose or load the extruded polymer tube 220 into a cylindrical form or mold 224. Mold 224 will be understood by a skilled artisan to be made of any preferable material to form a processing environment for the tube 220. In one embodiment, the mold 224 is made from brass. Mold 224 has mold ends 234A and 234B located on either side of the mold 224. The extruded polymer tube 220 has polymer tube ends 222A and 222B that will be disposed through the mold beyond the mold ends 234A and 234B, respectively.

Mold 224 also may have a plurality of stationary heating elements 226 disposed around the circumference of the mold. Therefore, when the tube 220 is disposed in the mold, the tube 220 may also have the stationary heating elements positioned about it. In one embodiment, these heating elements are preferably electrical heating elements. The mold 224 has an interior space 228 that is initially vacant of any polymer material.

In step 204, the polymer tube ends 222A and 222B may be clamped outside, or at the end portions, of the mold. A skilled artisan will understand that any known means in the art to secure or clamp the tube is envisioned by this process. Stationary heating elements 226 conduct heat transfer to the mold 224 via metal to metal heat conductivity. They further radiate heat from the mold 224 onto and around the extruded polymer tube 220 in the direction of arrows 232A and 232B.

It will be understood that the mold may be heated or cooled to any temperature necessary to perform tube processing. In the case that the mold is heated or cooled, the temperature in the mold may be any temperature necessary or any time period required to change the temperature of the polymer tube. For example, stationary heating elements 226 could heat the mold to one temperature, which in turn heats the polymer tube to a different temperature. One skilled in this art will understand that the temperature in the mold or the time taken to heat the mold may vary as necessary to hit the target temperature of the polymer tube.

In step 204, the user may heat the extruded polymer tube 220 to a first temperature, which would be between or in the range of its $T_g$ to its $T_{cc}$. When the polymer material is PLLA, the $T_g$ may be between about 60° C. to about 70° C. and the $T_{cc}$ may be between about 90° C. to about 110° C. For PLLA, $T_m$ is between about 165° C. to about 175° C. In one embodiment, the step of heating the extruded polymer tube may include heating the extruded polymer tube 220 to a first temperature being between about the $T_g$ and about the $T_{cc}$ of the polymer material. This may be about 74° C. Alternatively, the tube may be heated higher to a temperature of about 80° C. to about 90° C. Whichever temperature the user chooses for step 204, it will be understood that the temperature may be optionally changed at a later step to a different temperature as will be discussed further in detail below.

In step 206, the user longitudinally strains the extruded polymer tube 220 from the initial length $L_1$ to an extended length $L_2$, the tube 220 being within the mold. As a point of reference, the clamp may move the extruded polymer tube bi-directionally from positions 230A and 230B to positions 242A and 242B, respectively. This may apply a strain in the direction of arrows 240A and 240B, which longitudinally strains the tube from its initial length $L_1$ to its extended length $L_2$. In its extended length $L_2$, the tube ends are disposed farther outside of mold 224 at positions 238A and 238B from positions 222A and 222B, respectively.

This longitudinal strain may induce crystal and polymer chain orientation of amorphous domains in the longitudinal direction. In addition, the overall crystallinity of the extruded polymer tube may increase with the longitudinal strain. In one embodiment, the overall crystallinity of the polymer tube may increase from its initial crystallinity to an increased crystallinity. For example, initially the tube may have less than about 5% crystallinity. The longitudinal strain may increase the crystallinity to approximately 34% overall.

The strain applied in the directions of arrows 240A and 240B may strain the tube and increases its length from $L_1$ to $L_2$, which may include straining the extruded polymer tube to the extended length being about 20% to about 200% greater than the initial length. Because ultimately the user may seek to decrease the strain induced crystal orientation along the longitudinal axis, the longitudinal strain during this step may be kept to a minimum.

After step 206, the user may optionally include a cooling step to decrease the temperature. This method may include cooling the extruded polymer tube 220 to a second temperature being the same as or different from the first temperature. For example, the second temperature may be below the first temperature and above the $T_g$. Because the method allows a sequential strain, first, in a longitudinal direction and, second, in a radial direction, a skilled artisan will understand that the temperature can be changed between these steps. In one embodiment, the same temperature may be preferred for both longitudinal strain and the radial expansion. In one embodiment, this temperature is 74° C. Here, there is no temperature decrease between steps 206 and 208.

In an alternative embodiment, it may be preferred to use different temperatures for the longitudinal strain and the radial expansion. Longitudinal straining the tube at higher temperature may result less strain induced crystal orientation along the longitudinal axis. This process could also be used to obtain an isotropic material (having the same properties in two or more directions). In one embodiment, it is preferred to cool the tube from a first temperature in step 204 of about 90° C. to a second temperature of about 74° C. after step 206. In this embodiment, the second temperature is about 10° C. higher than the $T_g$ for the polymer material. A skilled artisan will understand different temperatures may be used while still performing both the radial expansion and the longitudinal strain between the $T_g$ and $T_{cc}$ of the polymer material.

In step 208, after longitudinally straining the extruded polymer tube 220, the user may pressurize the lumen 246 with a gas, increasing from a first pressure to a second pressure. This creates a pressure change from the first pressure being about atmospheric pressure to a second pressure being about two (2) bar to about twenty-five (25) bar. In one embodiment, the gas used to create the pressure in step 208 may be blown in through a hose in the direction of arrows 244A and 244B. Alternatively, the gas may be blown in through only one hose, either in the direction of 244A or 244B, while sealing off the other end completely without a hose. In one embodiment, the preferred gas is compressed nitrogen.

In step 210 in FIG. 3B, the pressure created in step 208 causes the extruded polymer tube 220 to radially expand in the directions of arrows 250, from an initial diameter $D_1$ to its expanded diameter $D_2$. The tube in the mold may expand all at once or "puff up." Overall, this process may create more uniform, homogeneous expansion of the tube by performing the radial expansion all at once. This may also be assisted by the stationary heating elements.

This radial expansion may induce or lead to a higher degree of polymer chain orientation in the circumferential direction. The polymer tube may gain improved mechanical properties through processing. If the degree of radial expansion is higher than the degree of longitudinal strain, the mechanical properties may be the highest in the circumferential direction, and there may be less crystal orientation along the longitudinal axis relative to the circumferential direction. This could change if the longitudinal strain is higher than the radial expansion. However, the total crystallinity of the polymer tube is not dependent on the degree of expansion. The total expansion may be 335% to 435%

Preferably, each step of the axial strain and radial expansion occur in about a few milliseconds, in steps 206 and 210 respectively. This may result in a time span between the longitudinal strain and the radial expansion of a few milliseconds or longer. A skilled artisan will understand that a sequential process may allow the user to tailor each step as desired.

In step 212, the longitudinally strained and radially expanded tube is cooled to a third temperature, creating or defining a processed polymer tube with increased mechanical properties. The pressure created in step 208 may be maintained constant until tube 222 is cooled in step 212. The tube is cooled below its $T_g$ to allow the polymer tube to retain integrity. At this point, the tube may no longer be soft.

In step 214, the processed polymer tube 254 having axis 251 may be cut to define a medical device. This processing involves removing or cutting off the unprocessed portions made up of the extruded polymer tube ends 222A and 222B. This also includes further processing of the tube. A skilled artisan will understand that this further processing may include annealing, heat setting, or laser cutting the process polymer tube into a desired pattern for a given medical device. In particular, this process polymer tube can be used for stent or filter applications.

In stent applications, the process polymer tube may have improved mechanical properties to maintain vessel patency against compressive loads. Alternatively for filter applications, the mechanical strength of the processed polymer tube may aid in engaging the vessel wall through sufficient frictional forces to keep its integrity and prevent device migration when placed in the vasculature.

Figure 4:
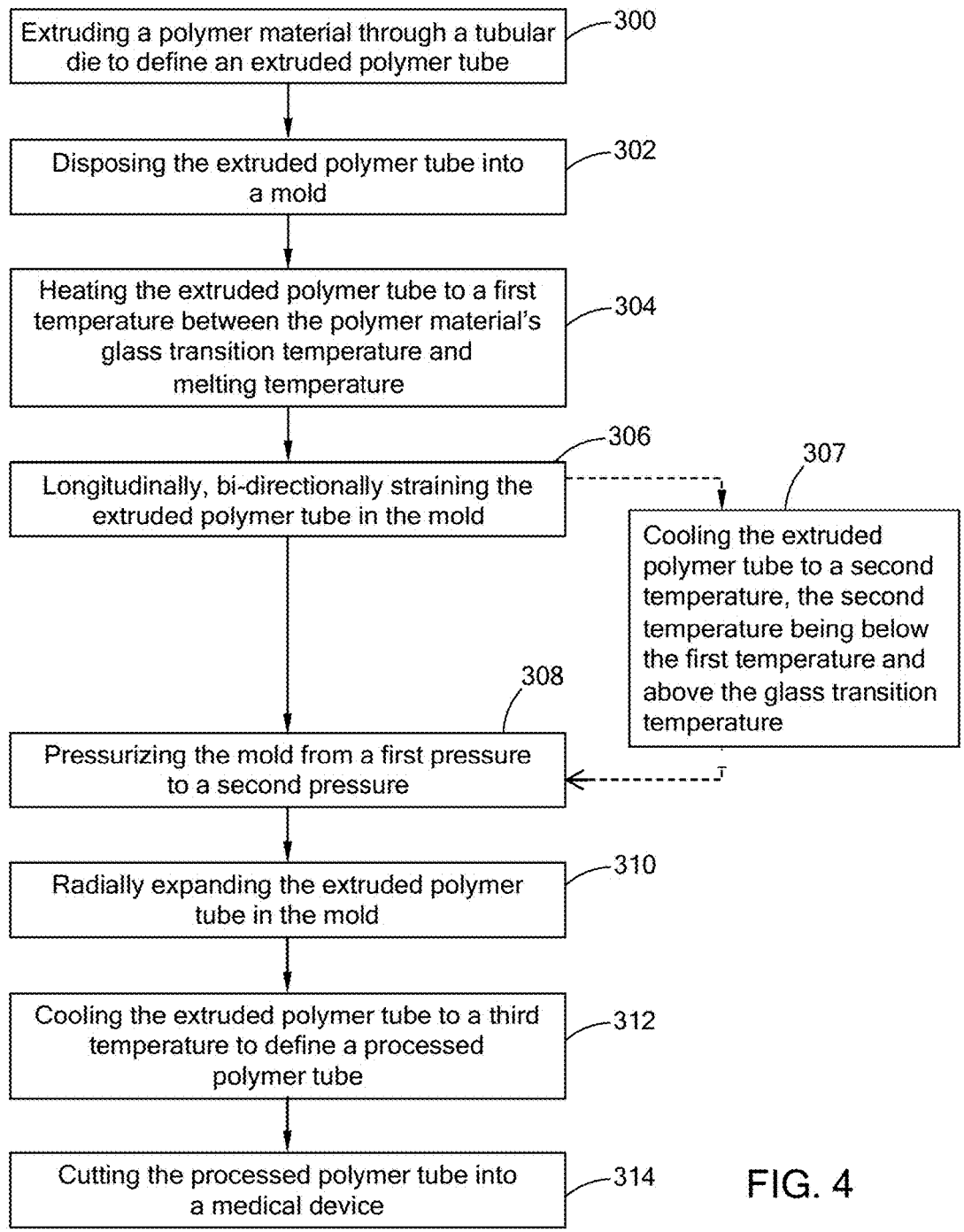
FIG. 4 is an expanded flow diagram of the sequential biaxial strain method of FIGS. 3A-B.

FIG. 4 shows an expanded flow diagram of the sequential biaxial strain method. In step 300, the user may extrude a polymer material through a tubular die to define an extruded polymer tube. In step 302, the user may dispose the extruded polymer tube into a mold. In step 304, the user heats the extruded polymer tube to a first temperature between the polymer material's glass transition temperature and cold crystallinity temperature. In step 306, the user longitudinally strains the extruded polymer tube within the mold.

In optional step 307, the tube may be cooled to a second temperature, this second temperature being below the first temperature and above the glass transition temperature. Whether taking this optional step 307 or not, the user in step 308 may pressurize the lumen, while the tube is inside the mold, from a first pressure to a second pressure. In step 310, the user may radially expand the polymer tube in the mold. In some embodiments, radially expansion of the extruded polymer tube may include expanding the initial diameter about 100% to about 500% to the expanded diameter. In step 312, the user may cool the extruded polymer tube to a third temperature to define a processed polymer tube. In step 314, the user may cut the process polymer tube into the desired medical device, either for a stent or filter applications as discussed above.

Experimental Data

FIGS. 5-16 show experimental data for tube processing discussed herein. In particular, these figures show comparison data for semi-crystalline tubes processed by different processing methods.

Experimental Conditions

In a first method, semi-crystalline tubes are processed using a sequential biaxial straining method, as described in this disclosure. In contrast, in a second method, semi-crystalline tubes are processed using a simultaneous biaxial straining method ("SIM"). Generally with the simultaneous method, the tubes are longitudinally strained and radially expanded at the same time. The purpose of this data is to compare the mechanical properties of tubes process by these two methods. In addition, tubes were uniaxially strained along the axial direction ("UNI") for comparison to both SEQ and SIM processing. More detailed experimental conditions are described below.

1. Sequential Method ("SEQ")

In this method, the inventors extruded a pure PLLA polymer tube having initial crystallinity of less than 5% (using 2003D pellets heated to 194° C. having initial crystallinity of less than 5%). The tube was placed in the mold and heated to a first temperature of about 74° C., above the glass transition temperature for PLLA. The tube was longitudinally, bi-directionally strained between about 20% to about 200% overall, at a rate of about 100 mm/s. There was no cooling step in this experimental data. Next, the tube is radial expanded. After radially expanding, the tube was cooled to a third temperature being room temperature. Subsequently, the processed tube was cut into circumferential rings for testing.

A skilled artisan will understand that the sequential method experiment could be performed with the optional step (shown in FIG. 4, step 307) where the tube was (1) heated to a first temperature of preferably about 80° C. to about 90° C.; (2) longitudinally strained; (3) cooled in step 307 to a second temperature of about 74° C.; and (4) then radially expanded.

2. Simultaneous Method ("SIM")

In this method, the inventors also extruded a pure PLLA polymer tube having initial crystallinity of less than 5% (using 2003D pellets heated to 194° C. having initial crystallinity of less than 5%). The tube was placed in the mold and heated to a first temperature of about 74° C., above the glass transition temperature for PLLA. The tube was longitudinally strained and radially expanded at the same time. The longitudinal strain occurred between about 20% to about 200% overall, at a rate of about 100 mm/s. There was no optional cooling step in this experimental data. After the straining step, the tube was cooled to a third temperature, being room temperature. Subsequently, the processed tube was cut into circumferential rings for testing.

Mechanical Testing

FIGS. 5A-B depict stress/strain curves for the processed tubes, measured in the circumferential direction. FIGS. 6A-B depict stress strain curves for processed tubes, measured in the axial direction. The x-axis of all graphs shows overall strain applied to the tubes (c). The y-axis of all graphs depicts stress of tubes ($\sigma$), calculated by the load experienced divided by cross sectional area. The key of each graph represents total area expansion (axial strain; radial strain).

FIG. 5A is a graph with curves for tubes processed with the Simultaneous Method. FIG. 5B is a graph with curves for tubes processed with the Sequential Method. As shown, elongation at rupture is improved with degree of axial strain, when keeping the radial strain constant.

By contrast, FIG. 6A is a graph with curves for tubes processed with the Simultaneous Method. FIG. 6B is a graph with curves for tubes processed with the Sequential Method. In FIGS. 5A-B, all tubes exhibit strain hardening, while the strain hardening effect is not detected in the axial direction (see FIGS. 6A-B), which shows a maximum stress value before 10% strain.

At the same time, the slope of the strain hardening region becomes steeper with total area expansion. In general, more variation was detected for samples with a high degree of strain (1.0; 3.2, all graphs), yet a larger fracture strength was detected when increasing the strain both axially and radially. Unlike the circumferentially tested tubes, elongation at fracture in the axial direction varied and did not occur over the entire gauge length, but failed in a localized area.

Figure 7:
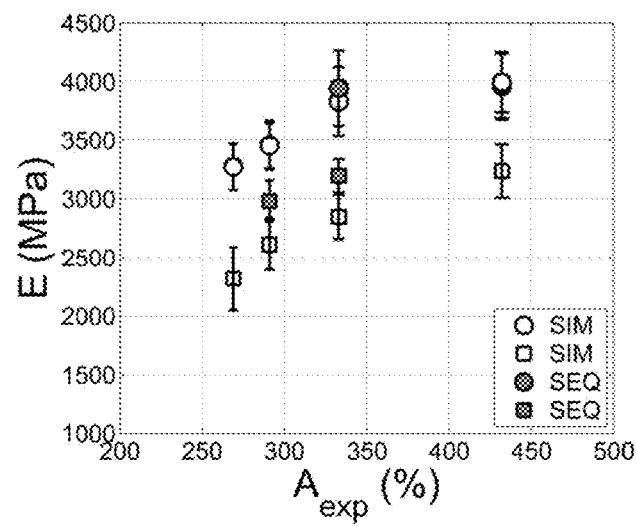
FIG. 7 depicts an elastic modulus comparison graph of semi-crystalline tubes processed by both simultaneous and sequential biaxial strain methods.

FIG. 7 shows an elastic modulus comparison graph of semi-crystalline tubes processed by both the simultaneous and sequential biaxial strain methods. In this graph, the x-axis shows the total area expansion percentage. This is the degree of expansion in both of the longitudinal and radial directions, along these axes. The y-axis shows the elastic modulus, which is the degree to which the processed polymer tube may be non-permanently or elastically deformed upon an applied force.

As shown in the legend, open circles represent data points for mechanical properties in the circumferential direction of tubes processed using the Simultaneous Method. Open squares represent data points for mechanical properties in the axial direction of tubes processed using the Simultaneous Method. Shaded circles represent data points for mechanical properties in the circumferential direction of tubes processed using the Sequential Method. Shaded squares represent data points for mechanical properties in the axial direction of tubes processed using the Sequential Method. Each data point has associated standard deviation error bars to show statistical significance.

Tubes processed by the Sequential Method may show improved mechanical properties over those processed with the Simultaneous Method. For example in FIG. 7 seen in data points with a total area expansion of about 335% and about 435%, the elastic modulus is statistically the same for tube strength (1) in the circumferential direction processed with the Simultaneous Method (open circles); (2) in the axial direction processed with the Sequential Method (shaded squares, only with 435% expansion); and (3) in the circumferential direction processed with the Sequential Method (shaded circles).

However, the elastic modulus is lower in the axial direction for tubes processed with the Simultaneous Method (open squares). Tubes processed under the Simultaneous Method and measured in the axial direction show lower elastic modulus at all expansion percentages, demonstrating possible improved elastic deformation.

Figure 8:
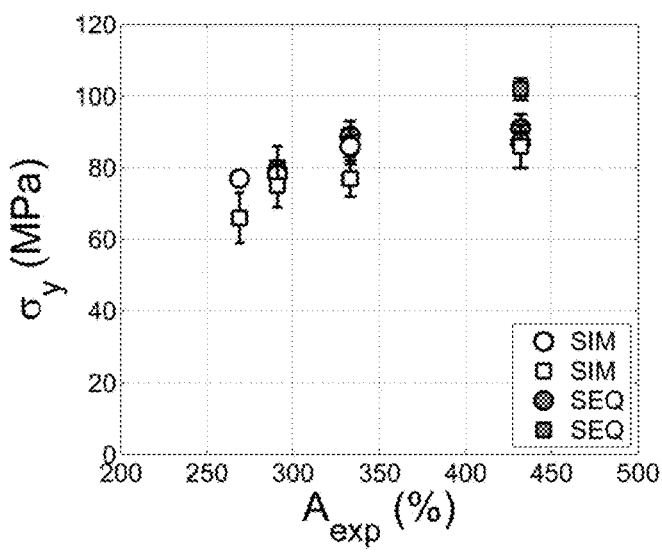
FIG. 8 depicts a graph of yield stress ($\sigma_y$) of processed tubes.

FIG. 8 depicts yield stress ($\sigma_y$) of processed tubes. The x-axis shows total area expansion, and the y-axis shows yield stress. As with FIG. 7, the legend shows open circles and squares for SIM processing, and shaded circles and squares for SEQ processing. Yield stress increased with the degree of strain in both directions, regardless of processing method. The yield stress in the axial direction for SEQ biaxially strained samples showed higher values than samples processed with the SIM Method at the highest expansion value.

FIG. 9 is a table depicting values for the elastic modulus, $\sigma_y$, $\sigma_{max}$ in both circumferential (circ) and axial direction. In the axial direction, $\sigma_y$ and $\sigma_{max}$ are the same. Statistical significance difference (level of 5%) between one total area expansion to another is denoted by either [a] showing significance difference from (0.5; 2.6), and [b] showing significance difference between SIM and SEQ biaxial strain for same total area expansion. As with FIGS. 5A-B, the parentheticals represent (axial strain; radial strain).

For example, FIG. 9 depicts that the tubular body processed with the SEQ method (1.0; 3.2) has an elastic modulus along the axial or longitudinal axis of above 3500 megapascals, more specifically about 4000 megapascals.

Being able to change the temperature between processing steps may allow for better tailoring of mechanical properties. SEQ processing (1.0; 3.2) results in a yield stress along the axial or longitudinal axis of above 90 megapascals, more specifically about 100 megapascals. Performing SEQ processing allows for a change in temperature or strain speed between longitudinal and radial strains, giving greater control over crystal formation.

As discussed herein, SEQ processing may involve forming a medical device having a tubular body wherein the tubular body is formed from an extruded polymer tube that is longitudinally strained in a mold. The extruded polymer tube may have an initial diameter, an initial length, and a lumen therethrough along a longitudinal direction or axis, wherein the extruded polymer tube is longitudinally strained from the initial length to an extended length. Subsequently, the extruded polymer tube may be radially expanded in the mold wherein the extruded polymer tube is expanded from the initial diameter to an expanded diameter.

Crystallinity

FIG. 10 depicts crystallinity percentages ($X_c$) and crystallite sizes for both the circumferential ($D_c$) and the axial direction ($D_a$). As seen in FIG. 10, the uniaxial strain (1.0; 0) allows formation of the highest degree of crystallinity ($X_c$) (34% and subsequent heating allows a formation of 36% crystallinity). The SEQ and SIM biaxially strained samples showed overall no difference (29-32%). This effect is further demonstrated with Differential Scanning calorimetry ("DSC") data in FIG. 11. Further, UNI with axial strain at 0.2 and 0.5 did not induce any crystallinity (data not shown).

In addition, the $T_g$ did not change significantly as a function of area expansion for SEQ biaxial straining. However, there is a slight increase in $T_g$ for SIM biaxial strain. During heating of the SEQ and SIM biaxial samples for 60 min at 90° C., no cold crystallization top appear, despite the crystallinity being far from the maximum crystallinity degree of PLLA. In addition, FIG. 10 shows that the $X_c$ is not dependent on the ratio between axial and radial strain; it remains fairly constant.

Orientation

Figure 11:
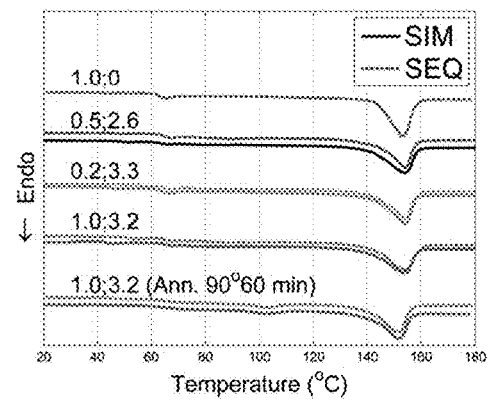
FIG. 11 depicts heating curves of processed tubes.
Figure 12:
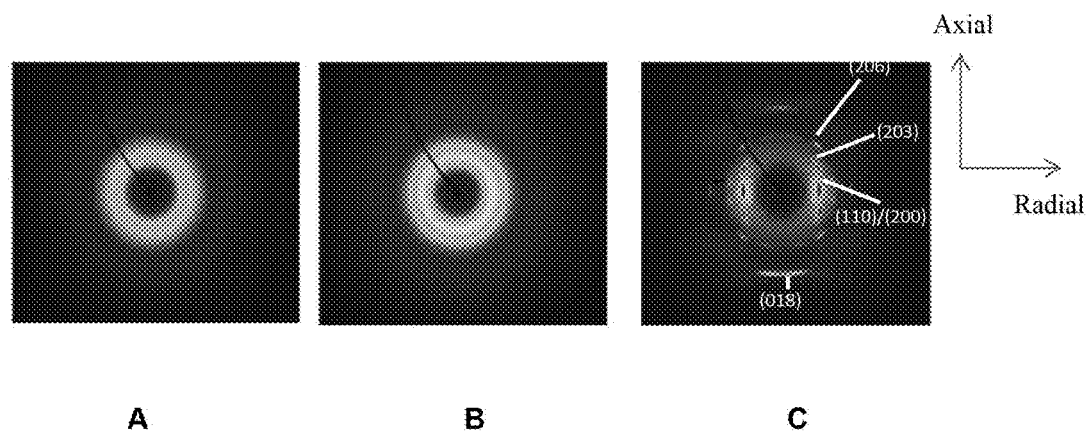
FIG. 12 depicts wide angle x-ray scattering ("WAXS") images of processed tubes.

FIG. 11 depicts heating curves of processed tubes. For example, PLLA strained tubes processed either UNI strain, SIM, or SEQ biaxially strained tubes with or without post-annealing at 90° C. for 60 min. The axial and radial strain is given parentheses separated by semicolon (εa; εr).

FIGS. 12A-C depict WAXS images of partially processed tubes. These samples were examined using a 2D diffraction setup equipped with a rotating anode Cu Kα X-ray source, monochromated and focused by 1D multilayer optics ($\lambda$=1.5418 Å), operated at 50 kV and 200 mA. A tube sample was cut in half and placed perpendicular to the beam. The distance between detector and sample was 123 mm. The measurement duration was 30 minutes.

FIG. 12A shows raw material, 12B shows heating raw material to 74° C. on the inside (inside, first temperature), and FIG. 12C shows heated material after 96% axial strain. FIG. 12C includes the most reflection planes for strain-induced PLLA. The WAXS pattern in FIG. 12C shows highly ordered α crystals by sharp reflections in the (110/200) plane. As expected, the raw material in FIG. 12A showed virtually no crystallinity after tube extrusion. Upon heating, no crystallites are formed and the tube remains low in crystallinity.

FIG. 12B shows isotropic amorphous material by the diffuse amorphous halo, which is confirmed by DSC. Uniaxial straining at 74° C. induces crystallinity up to 34% (shown in FIG. 12C), and is possible when the strain is nearly 100%. Strain below this does not induce any notable crystallinity, as axial strain of 24-68% only induced crystallinity of 2.4%. As expected, the crystal orientation remains in one direction. However, the orientation is turned 90° compared to the other stretching schemes. The (110)/(200) direction is now parallel to radial direction rather than the axial direction.

Figures 13, 14:
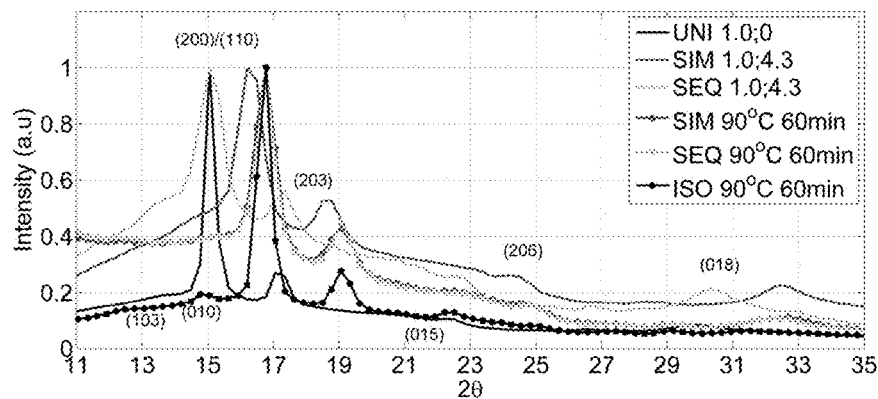
FIG. 13 is a table depicting scattering angles for processed tubes.
FIG. 14 is an intensity graph of processed tubes.

FIG. 13 depicts scattering angles for processed tubes. For example, scattering angles (2θ) and their crystal planes for PLLA after ISO crystallization, UNI axial, SIM, and SEQ biaxial strain, before and after or annealing. Isothermal (ISO) crystallization is an additional method that can be performed to improve polymer properties, but often must be performed at high annealing temperature and/or durations unfavorable for production in the industry. ISO crystallization data has been provided here for comparison. In addition for comparison, the scattering angles for α and α'-crystals according to the literature are listed (chen et al 2011, wang et al 2006). The axial and radial strain is given in parentheses separated by semicolon ($\varepsilon_a$; $\varepsilon_r$).

Scattering occurs in multiple planes, as shown in FIG. 13, including the planes corresponding to the most commonly occurring reflections for PLLA (103), (010), (110/200), (203), (015) and (207). In this study, ISO crystallization shows diffraction peaks solely as α-crystals in (103), (110)/(200), (203), (206) and (015). In contrast, UNI strain shows peaks at lower 2θ indicating α'-crystals, while lacking the peak for the (103) plane and having the additional (018) plane peak. The shift in 2θ could be the higher crystallization temperature, $T_c$=90° C. in ISO crystallization, whereas in UNI strain the $T_c$=74° C.

All (203), (206) and (018) are visible in SIM and SEQ, in accordance with reflections of α'-crystals with a larger interplanar spacing. The inventors conclude that these reflections are only visible for strain induced crystallization. Both SIM and SEQ biaxial strain shows diffraction peaks corresponding to the (110/200) planes at lower 2θ than for the α-crystals seen for ISO crystallization.

FIG. 14 depicts an intensity graph of the processed tubes. This shows intensity plots for (1) UNI at 96% strain; (2) ISO crystallization at 90° C. for 60 min; (3) SIM and (4) SEQ biaxial strain at the axial to circumferential ratio of 1.0×4.3 strain; both (5) before and (6) after post annealing for 60 min at 90° C. Note that the latter two have a large background scattering. The axial and radial strain is given in parentheses separated by semicolon ($\varepsilon_a$; $\varepsilon_r$). In FIG. 14, X-ray diffraction patterns are identical for both SEQ and SIM biaxial strain, but SEQ biaxial strain peaks are shifted towards lower scattering angles (2θ).

Figures 15, 16:
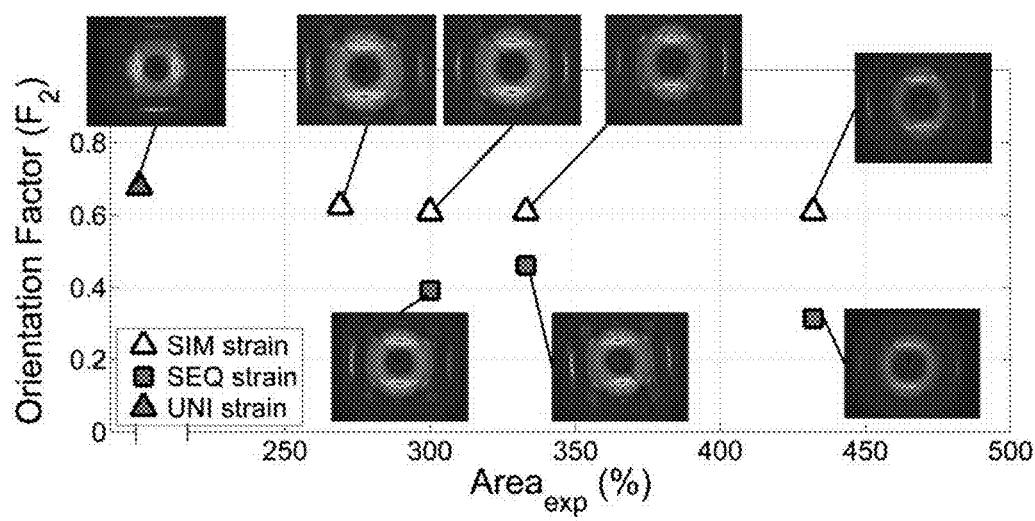
FIG. 15 is depicts orientation factors and WAXS images for processed tubes.
FIG. 16 is a table comparing crystallinity of semi-crystalline tubes processed by both simultaneous and sequential biaxial strain methods.

FIG. 15 shows an x-ray scattering comparison graph of semi-crystalline tubes processed by both simultaneous and sequential biaxial strain methods. FIG. 15 also shows WAXS images at each data point. In this graph, the x-axis shows the total area expansion percentage. This is the degree of expansion in both the longitudinal and radial directions. The y-axis shows the orientation factor, which is related to how highly oriented crystals are within the processed polymer tube. More highly oriented crystals may be more brittle, possibly yielding lower mechanical properties.

As shown in the legend, the open triangles represent data from a tube processed by the SIM Method. The shaded squares represent data from a tube processed by the SEQ Method. The shaded triangle represents data from a tube processed by only a longitudinal strain without a radial expansion.

Tubes processed by the SEQ Method have a lower orientation factor over other tubes in this experiment; thus, possible improved mechanical properties. For example, the longitudinally strained tube has an orientation factor of about 0.7, and the simultaneously strained tubes have orientation factors of about 0.6. In contrast, the SEQ stained tubes have a much lower orientation factor of about 0.3 to 0.4 depending on the degree of expansion, showing much lower crystal orientation.

While FIG. 15 shows that the SEQ Method gives a lower orientation factor, FIG. 16 shows that the overall crystallinity of the tubes is approximately the same. FIG. 16 shows a degree of crystallinity comparison table of semi-crystalline tubes processed by both simultaneous and sequential biaxial strain methods. The crystallinity percentage ($X_c$) was accessed after processing a tube with the Simultaneous Method, after the longitudinal/axial strain with the SEQ Method, and after the radial expansion with the Sequential Method. After only the axial strain with the Sequential Method, the $X_c$ was about 34%. After processing with the Sequential Method to a total area expansion of about 432%, the $X_c$ decreased to about 29%. After processing with the Simultaneous Method to a total area expansion of about 432%, the $X_c$ decreased to about 30%.

Based on these results, the $X_c$ for both processing methods is about the same. However, based on the data in FIG. 15, the inventors believe that the orientation of that $X_c$ is different for both the Simultaneous and Sequential Method. While both methods show similar overall crystallinity, the Sequential Method gives lower crystal orientation than the Simultaneous Method. Lower crystal orientation may lead to advantages in withstanding structural loads. As seen, the SEQ method may give the ability to tailor and modify the polymer structure by performing sequential strains in a manner that SIM processing may not allow for with simultaneous strains. Steps in the SEQ method could be tailored as necessary to achieve a wide variety of characteristics and/or advantages in processing a polymer.

It should be understood that the above disclosure of the process for sequential biaxial strain of semi-crystalline tubes is merely exemplary of these processing steps, and is not intended to limit the scope of the disclosure. Other steps, parts, assemblies and methods may be used without falling beyond the scope and spirit of the present disclosure as defined in the following claims.

The invention claimed is:

1. A method of processing a polymer, the method comprising:
heating an extruded polymer tube to a first temperature in a mold comprising a plurality of stationary heating elements, the first temperature being between a glass transition temperature and a cold crystallinity temperature of the polymer, the extruded polymer tube having an initial diameter, an initial length, and a lumen therethrough along a longitudinal direction, and longitudinally straining the extruded polymer tube from the initial length to an extended length; and
after the step of longitudinally straining an extruded polymer tube, radially expanding the extruded polymer tube in the mold wherein the extruded polymer tube is expanded from the initial diameter to an expanded diameter.

2. The method of claim 1 wherein the step of longitudinally straining an extruded polymer tube comprises straining the extruded polymer tube to the extended length being about 20 percent to about 200 percent greater than the initial length.

3. The method of claim 1 further comprising extruding a polymer material through a tubular die to define the extruded polymer tube before the step of longitudinally straining an extruded polymer tube.

4. The method of claim 3 further comprising disposing the extruded polymer tube into the mold before the step of longitudinally straining an extruded polymer tube.

5. The method of claim 4 wherein the step of disposing the extruded polymer tube comprises positioning the plurality of stationary heating elements circumferentially about the extruded polymer tube.

6. The method of claim 1, wherein the step of heating the extruded polymer tube comprises heating the extruded polymer tube to the first temperature being between about 74° C. and about 90° C.

7. The method of claim 1, wherein the step of heating the extruded polymer tube comprises heating the extruded polymer tube to the first temperature being about 90° C.

8. The method of claim 1, further comprising cooling the extruded polymer tube to a second temperature after the step of longitudinally straining an extruded polymer tube and before the step of radially expanding the extruded polymer tube.

9. The method of claim 8 wherein the step of cooling the extruded polymer tube comprising cooling the extruded polymer tube to the second temperature being below the first temperature and above the glass transition temperature.

10. The method of claim 9 wherein the step of cooling the extruded polymer tube comprises cooling the extruded polymer tube to the second temperature being about 74° C.

11. The method of claim 1 further comprising pressurizing the lumen after the step of longitudinally straining an extruded polymer tube and before the step of radially expanding the extruded polymer tube, the step of pressurizing comprises increasing from a first pressure to a second pressure with a gas.

12. The method of claim 11 wherein the step of pressurizing the lumen comprises pressurizing the lumen from the first pressure being about atmospheric pressure to the second pressure being between about 2 bar and about 25 bar.

13. The method of claim 8 further comprising cooling the extruded polymer tube to a third temperature, defining a processed polymer tube, the step of cooling the extruded polymer tube being after the step of radially expanding an extruded polymer tube.

14. The method of claim 13 further comprising cutting the processed polymer tube to define a medical device.

15. The method of claim 1 wherein the step of radially expanding the extruded polymer tube comprising expanding the initial diameter about 100% to about 500% to the expanded diameter.

* * * * *